(12) United States Patent
Piletsky et al.

(10) Patent No.: US 11,796,545 B2
(45) Date of Patent: Oct. 24, 2023

(54) METHODS AND KITS FOR DETERMINING BINDING SITES

(71) Applicant: University of Leicester, Leicester (GB)

(72) Inventors: Sergey Piletsky, Leicester (GB); Elena Piletska, Leicester (GB); Francesco Canfarotta, Leicester (GB); Don Jones, Leicester (GB)

(73) Assignee: University of Leicester

( * ) Notice: Subject to any disclaimer, the term of this patent is extended or adjusted under 35 U.S.C. 154(b) by 821 days.

(21) Appl. No.: 16/497,684

(22) PCT Filed: Mar. 19, 2018

(86) PCT No.: PCT/GB2018/050707
§ 371 (c)(1),
(2) Date: Sep. 25, 2019

(87) PCT Pub. No.: WO2018/178629
PCT Pub. Date: Oct. 4, 2018

(65) Prior Publication Data
US 2020/0033356 A1    Jan. 30, 2020

(30) Foreign Application Priority Data

Mar. 27, 2017   (GB) .................... 1704823

(51) Int. Cl.
*G01N 33/68* (2006.01)
(52) U.S. Cl.
CPC ..... *G01N 33/6845* (2013.01); *G01N 33/6818* (2013.01); *G01N 33/6878* (2013.01)
(58) Field of Classification Search
None
See application file for complete search history.

(56) References Cited

U.S. PATENT DOCUMENTS

| | | |
|---|---|---|
| 2004/0058006 A1 | 3/2004 | Barry et al. |
| 2004/0185506 A1 | 9/2004 | Heavner |
| 2013/0137117 A1 | 5/2013 | Levi et al. |

FOREIGN PATENT DOCUMENTS

| | | |
|---|---|---|
| EP | 2132549 A1 | 12/2009 |
| JP | 2002-286724 | 10/2002 |
| WO | 0188538 A2 | 11/2001 |
| WO | 2004092741 A2 | 10/2004 |
| WO | WO 2008/119488 | * 10/2008 |

OTHER PUBLICATIONS

Chaves et al., "In-tube solid-phase microextraction with molecularly imprinted polymer to determine interferon alpha 2a in plasma sample by high performance liquid chromatography", Journal of Chromatography A, 2013.
Tai et al., "Artificial-epitope mapping for CK-MB assay", Analyst, 2011, 136, 2230.
Komarova et al., "Design of molecularly imprinted conducting polymer protein-sensing films via substrate-dopant binding", Analyst, 2015, 140, 1099.
Francesco Canfarotta et al., "Biocompatibility and internalization of molecularly imprinted nanoparticles", Nano Research, Jul. 2016.
Detlev Suckau et al., "Molecular epitope identification by limited proteolysis of an immobilized antigen-antibody complex and mass spectrometric peptide mapping", Proc. Natl. Acad. Sci. USA, Dec. 1990, pp. 9848-9852, vol. 87.
Dr. Antonio Guerreiro et al., "Influence of Surface-Imprinted Nanoparticles on Trypsin Activity", Advanced Healthcare Materials, DE, (Mar. 20, 2014), vol. 3, No. 9, doi:10.1002/adhm. 201300634, ISSN 2192-2640, pp. 1426-1429, XP055799200.
Hidekazu Nishino et al., "Selective Protein Capture by Epitope Imprinting", Angewandte Chemie International Edition, (Apr. 3, 2006), vol. 45, No. 15, doi: 10.1002/anie.200503760, ISSN 1433-7851, pp. 2392-2396, XP055009776.
Katarzyna Smolinska-Kempisty et al., "A comparison of the performance of molecularly imprinted polymer nanoparticles for small molecule targets and antibodies in the ELISA format", Scientific Reports, (Nov. 24, 2016), vol. 6, No. 1, doi:10.1038/srep37638, XP055473610 [A] 1-33.
Lingxin Chen et al., "Molecular imprinting: perspectives and applications", Chemical Society Reviews, (Jan. 1, 2016), vol. 45, No. 8, doi:10.1039/C6CS00061D, ISSN 0306-0012, pp. 2137-2211, XP055473665 [A] 1-33.

* cited by examiner

*Primary Examiner* — Christopher M Gross
(74) *Attorney, Agent, or Firm* — Aura IP Law, PC (57) ABSTRACT

The invention provides methods, compositions, and kits for the characterisation and analysis of proteins. Methods are provided for determining, on a protein, a binding site for a binding partner, the methods comprising: contacting a protein with a plurality of monomers, and polymerising the monomers to create a protein:polymer complex; digesting the protein in the complex to produce a peptide:polymer complex; isolating the peptide:polymer complex; and sequencing the peptide, wherein the peptide corresponds to a binding site for a binding partner.

13 Claims, 1 Drawing Sheet
Specification includes a Sequence Listing.

SEQUENCE LISTING

```
<160> NUMBER OF SEQ ID NOS: 15

<210> SEQ ID NO 1
<211> LENGTH: 18
<212> TYPE: PRT
<213> ORGANISM: Electrophorus electricus

<400> SEQUENCE: 1

Leu Ala Leu Gln Trp Val Gln Asp Asn Ile His Phe Phe Gly Gly Asn
1               5                   10                  15

Pro Lys
```

```
<210> SEQ ID NO 2
<211> LENGTH: 8
<212> TYPE: PRT
<213> ORGANISM: Electrophorus electricus

<400> SEQUENCE: 2

Phe Arg Phe Ser Phe Val Pro Val
1               5

<210> SEQ ID NO 3
<211> LENGTH: 26
<212> TYPE: PRT
<213> ORGANISM: Electrophorus electricus

<400> SEQUENCE: 3

Gln Val Thr Ile Phe Gly Glu Ser Ala Gly Ala Ala Ser Val Gly Met
1               5                   10                  15

His Leu Leu Ser Pro Asp Ser Arg Pro Lys
            20                  25

<210> SEQ ID NO 4
<211> LENGTH: 8
<212> TYPE: PRT
<213> ORGANISM: Electrophorus electricus

<400> SEQUENCE: 4

Glu Asp Phe Leu Gln Gly Val Lys
1               5

<210> SEQ ID NO 5
<211> LENGTH: 15
<212> TYPE: PRT
<213> ORGANISM: Electrophorus electricus

<400> SEQUENCE: 5

Thr Gly Asn Pro Asn Ile Asn Val Asp Gly Ser Ile Asp Ser Arg
1               5                   10                  15

<210> SEQ ID NO 6
<211> LENGTH: 11
<212> TYPE: PRT
<213> ORGANISM: Electrophorus electricus

<400> SEQUENCE: 6

Arg Trp Pro Val Phe Thr Ser Thr Glu Gln Lys
1               5                   10

<210> SEQ ID NO 7
<211> LENGTH: 8
<212> TYPE: PRT
<213> ORGANISM: Homo sapiens

<400> SEQUENCE: 7

Phe Arg Phe Ser Phe Val Pro Val
1               5

<210> SEQ ID NO 8
<211> LENGTH: 7
<212> TYPE: PRT
<213> ORGANISM: Electrophorus electricus

<400> SEQUENCE: 8

Gly Glu Ser Ala Gly Ala Ala
1               5
```

<210> SEQ ID NO 9
<211> LENGTH: 7
<212> TYPE: PRT
<213> ORGANISM: Homo sapiens

<400> SEQUENCE: 9

Tyr Trp Ala Asn Phe Ala Arg
1               5

<210> SEQ ID NO 10
<211> LENGTH: 7
<212> TYPE: PRT
<213> ORGANISM: Homo sapiens

<400> SEQUENCE: 10

Leu Ala Leu Gln Trp Val Gln
1               5

<210> SEQ ID NO 11
<211> LENGTH: 17
<212> TYPE: PRT
<213> ORGANISM: Homo sapiens

<400> SEQUENCE: 11

Phe Gly Glu Ser Ala Gly Ala Ala Ser Val Gly Met His Leu Leu Ser
1               5                   10                  15

Pro

<210> SEQ ID NO 12
<211> LENGTH: 10
<212> TYPE: PRT
<213> ORGANISM: Homo sapiens

<400> SEQUENCE: 12

Leu Leu Asp Gln Arg Leu Ala Leu Gln Trp
1               5                   10

<210> SEQ ID NO 13
<211> LENGTH: 10
<212> TYPE: PRT
<213> ORGANISM: Homo sapiens

<400> SEQUENCE: 13

Thr Leu Phe Gly Glu Ser Ala Gly Ala Ala
1               5                   10

<210> SEQ ID NO 14
<211> LENGTH: 25
<212> TYPE: PRT
<213> ORGANISM: Homo sapiens

<400> SEQUENCE: 14

Lys Thr Val Thr Ile Phe Gly Glu Ser Ala Gly Gly Ala Ser Val Gly
1               5                   10                  15

Met His Ile Leu Ser Pro Gly Ser Arg
            20                  25

-continued

```
<210> SEQ ID NO 15
<211> LENGTH: 9
<212> TYPE: PRT
<213> ORGANISM: Homo sapiens

<400> SEQUENCE: 15

Val Phe Arg Phe Ser Phe Val Pro Val
1               5
```

METHODS AND KITS FOR DETERMINING BINDING SITES

CROSS REFERENCE TO RELATED APPLICATIONS

This application is a National Phase of International Application No. PCT/GB2018/050707, filed Mar. 19, 2018, and that International Application was published under PCT Article 21(2) in English. This application also includes a claim of priority to Application No. GB 1704823.2, filed Mar. 27, 2017, the entirety of which is hereby incorporated by reference.

The invention relates to the field of determining, on a protein, a binding site for a binding partner. The invention provides methods for determining a binding site for a binding partner, and kits for performing such methods.

Proteomics is the study of the structure and function of proteins expressed by cells and tissues, and it is of practical importance since proteins are the main targets for small drug molecules and therapeutic antibodies [1]. Identification of a protein's binding sites for antibodies can aid in the development of new diagnostics [2]. FDA and EMEA guidelines require molecular analysis of the interaction site between a drug and its target for the regulatory filing [3]. In addition, understanding of the binding site is useful to protect commercial products with patents. Unfortunately, defining protein structure in molecular detail and identification of binding sites constitutes a particularly difficult task.

The part of the protein which binds specifically to antibodies, B cells, or T cells is called an epitope. An antibody interacts with an epitope by virtue of non-covalent interactions between the amino acid sequences of the antibody and epitope, and the process of identifying epitopes for corresponding antibodies is called epitope mapping. Mapping epitopes by solving the structure of protein-antibody complexes can be achieved by X-ray crystallography and NMR analysis [4, 5, US2004185506 (HEAVNER GEORGE A)]. These techniques are, however, very laborious and expensive, as crystallography requires large amounts of antibodies of which the structure should be known, whilst NMR analysis requires knowledge of the structure of the antigen [2]. In addition, many protein-protein complexes prove unsuitable for NMR and X-ray analysis, and it is often difficult to make protein-antibody and peptide-antibody crystals [2, 6].

Alternatively, epitope mapping can be performed by combinatorial approaches, which can be achieved using peptide arrays with labelled antibodies bound to each peptide sequence. In the presence of the unknown (target) epitope from protein hydrolysate, antibodies are displaced, and posterior analysis of the array will allow identification of which antibodies were displaced and so the peptide sequence can be determined (WO 2001088538, DUMAS DAVID P). Other combinatorial approaches include screening a large set of peptides designed to cover all of the anticipated binding regions of a protein and finding the peptides which elicit an immune response (US2009226471, BENAROYA RES INST AT VIRGINIA). A similar approach uses immobilised antibodies which can bind to a target protein. A library of peptides in solution is then added to the immobilised antibodies, and once the peptides which bind to the immobilized antibodies are identified, sequences are computationally aligned with that of the whole target protein (WO 2004092741, UNIV MONTANA STATE). Other experimental methods commonly used include phage display and proteolysis of protein-antibody complexes combined with mass spectrometry [2, 7]. A problem with all existing experimental approaches for potential epitope mapping is that they require antibodies, which might not be available, or their quality and performance might not be sufficient for mapping.

Other methods that allow predicting the interactions between antibody-antigen and hence determination of potential epitopes are based on molecular modelling and computer simulation, like those described in US2014100834 (MACROMOLTEK). A large variety of in silico products for epitope screening has recently emerged [2], including software to screen antigens based on their genetic profile [8] and protein-protein docking methods based on B-cell epitope databases [9,], together with one-structure-based prediction tools [11]. Additional approaches include web-based tools which scan a whole antigen and can predict the most probable epitope regions [12].

However, these methods are not always accurate and require detailed information about protein structure. As an alternative, molecular imprinting methods have been used to assess if a small library of peptides were conformational epitopes of a protein (creatine kinase), and the method still required information about the protein and previous knowledge of the candidate epitope sequences [13].

There is therefore a need to provide improved methods and materials that may be used to determine, on a protein target, a binding site or epitope for a binding partner, such as an antibody or antigen binding fragment thereof.

The invention provides methods, compositions, and kits for the characterisation and analysis of proteins.

Hence, in a first aspect of the invention, there is provided a method for determining, on a protein, a binding site for a binding partner, comprising:
  contacting the protein with a plurality of monomers, and polymerising the monomers to create a protein:polymer complex;
  digesting the protein in the complex to produce a peptide:polymer complex; and
  isolating the peptide:polymer complex; and optionally sequencing the peptide, wherein the peptide corresponds to a binding site for a binding partner.

Advantageously, the method of the first aspect does not require information about protein structure or the availability of antibodies for experimental identification of peptide sequences which are binding site candidates. The characterisation and analysis may be for obtaining information related to amino acid sequences exposed on a protein surface. The information derived is useful for the identification of binding sites upon a protein, which may be suitable for the binding of binding partners, such as antibodies, aptamers, affimers, small drug molecules, MIPs or other natural or synthetic receptors. The information about these sequences may be obtained using molecular imprinting and sequencing techniques. Knowledge about these amino acid sequences may be used for generating binding partners, such as high affinity antibodies or other natural or synthetic receptors, for research, diagnostic, or therapeutic applications.

The protein upon which the method of the invention is performed, which may be referred to as the target protein, can be any molecule or composition comprising a component which comprises a chain of amino acid monomers or a peptide. The protein may be a single or multi-domain protein. The protein may be in a complex with other components, such as nucleic acids (DNA and/or RNA), cofactors, prosthetic groups, co-substrates, inorganic ions, vitamins, or sugars. The protein may include naturally occurring standard amino acids, naturally occurring non-standard amino acids, or non-naturally occurring amino acids. The protein may include modifications, including post-translational modifications or synthetic modifications. The protein may be a naturally occurring protein, or may be a protein not found in nature. The protein may be selected from the group consisting of: protein exposed on a cell surface, extracellular protein, intracellular protein, antibody, non-immunoglobulin protein, glycoprotein, phosphorylated protein, nucleoprotein, lipoprotein, glucosaminoglycan, mucoprotein, synthetic protein, or protein-DNA and protein-saccharide complexes. The protein may be a biomarker of a pathological state or a disease state. In some embodiments, two or more proteins may be used in a mixture or separately. Other embodiments may include an array of two or more proteins. In another embodiment, the protein is a complex with an enzyme inhibitor, drug molecular or other protein.

In a preferred embodiment, the protein is a folded protein comprising one or more sequence that is exposed on the protein surface and a buried sequence that is not exposed.

In some embodiments, the protein may be immobilised on a solid surface, such as a surface comprising polysaccharide, silica, organic or inorganic polymer, metal, or a combination thereof. For example, the solid surface may be in the form of beads, magnetic beads, arrays, the surface of waveguides, fibres, membranes, capillaries or any other surface suitable for the intended application. The immobilisation may be to assist in subsequent isolation steps, for instance the isolation of the protein:polymer complex disclosed herein.

The binding site to be determined may correspond to an amino acid sequence exposed on the surface of the target protein. The binding site may correspond to a region of the target protein that is capable of being bound by an antibody, an aptamer, an affimer, a small drug molecule, a MIP, a natural receptor, a synthetic receptor, or any combination thereof. The binding site may be an epitope, for example an epitope to which antibodies (i.e. binding partners) are capable of binding, or an epitope that interacts with B cells, and so in this case, the method may be described as a method of epitope mapping. The binding site may be a novel binding site, in that no prior knowledge of the binding site and/or the protein is required in order for the binding site to be identified by methods of the present invention.

A binding partner may be any molecule or composition that is capable of binding to the target protein. Potential binding partners include, but are not limited to, antibodies, aptamers, affimers, small drug molecules, MIPs, natural receptors, synthetic receptors, or any combination thereof.

The method of the invention involves contacting the target protein with a plurality of monomers. The plurality of monomers may be one type of monomer, or a mixture of different types of monomer. The polymerisation of the monomers may result in the creation of a molecularly imprinted polymer (MIP). The plurality of monomers or monomer mixture may take any form or composition suitable for the formation of a molecularly imprinted polymer. The contacting may be in any manner, or under any conditions, suitable for the formation of a molecularly imprinted polymer. The plurality of monomers may include monomers selected from the group: vinyl monomers, allyl monomers, acetylenes, acrylates, methacrylates, acrylamides, methacrylamides, chloroacrylates, itaconates, trifluoromethylacrylates, derivatives of amino acids, nucleosides, nucleotides, carbohydrates, or any combination thereof. The target protein may be in solution or immobilised on a solid surface when brought into contact with the plurality of monomers.

The solid surface for immobilisation of the target protein may be of any composition or form as disclosed herein.

The plurality of monomers may optionally include cross-linking monomers. Cross-linking monomers are optionally used to stabilise the structure of the resulting polymer, so that it remains bound to that of the protein target. Typical examples of cross-linkers suitable for the synthesis of polymer include, but are not limited to, ethylene glycol dimethacrylate, trimethylolpropane trimethacrylate, divinylbenzene, methylene bisacrylamide, ethylene bisacrylamide and N,N'-bisacryloylpiperazine. The function of cross-linking agents can be performed by particles or precursor polymers containing double bonds, or particles or polymers with multiple functionalities attached which can bind to functional monomers. Those skilled in the art could select monomers and cross-linkers suitable for a particular system.

There are a wide range of possible concentrations of monomers and combinations of monomers that would be suitable for use with the presently disclosed method. While potential ranges and sub-ranges are disclosed herein, the skilled person would be aware that these ranges are merely guides, and that any plurality of monomers suitable for use with the presently claimed method would be appropriate. For instance, the plurality of monomers or monomer mixture may take any form or composition suitable for the formation of a molecularly imprinted polymer.

The monomers may be present in a polymerisation mixture in an amount of from about 0.01 to 80% by weight, optionally from about 0.1 to 80% by weight.

The monomer mixture may be prepared in aqueous solution or in appropriate organic solvent. The solution or solvent may optionally comprise an initiator, and optionally buffer salts.

The concentration of each type of monomer may be varied depending on the intended final concentration in the reaction mixture. The following concentrations described for N-Isopropylacrylamide (NIPAM), methylene bisacrylamide (MBAA), tert-butylacrylamide, acrylic acid, or 3-aminopropyl methacrylate might, for example, be used to form a reaction mixture by the combination of 10 ml of monomeric mixture with 0.7 ml of a mixture comprising the target protein; this example is purely illustrative and is intended to indicate acceptable concentrations in final reaction volume.

The plurality of monomers may comprise NIPAM. The NIPAM may be present at 0.001 mg/ml to 100 mg/ml, 0.01 mg/ml to 10 mg/ml, 0.05 mg/ml to 5 mg/ml, or 0.1 mg/ml to 1 mg/ml.

The plurality of monomers may comprise methylene bisacrylamide (MBAA). The MBAA may be present at 0.0001 mg/ml to 10 mg/ml, 0.001 mg/ml to 5 mg/ml, 0.005 mg/ml to 0.5 mg/ml, or 0.01 mg/ml to 0.1 mg/ml.

The plurality of monomers may comprise tert-butylacrylamide. The tert-butylacrylamide may be present at 0.001 mg/ml to 100 mg/ml, 0.01 mg/ml to 10 mg/ml, 0.05 mg/ml to 5 mg/ml, or 0.1 mg/ml to 1 mg/ml.

The plurality of monomers may comprise acrylic or methacrylic acid. The acrylic or methacrylic acid may be present at 0.001 mg/ml to 100 mg/ml.

The plurality of monomers may comprise 3-aminopropyl methacrylate. The 3-aminopropyl methacrylate may be present at 0.0001 mg/ml to 10 mg/ml, 0.001 mg/ml to 5 mg/ml, 0.005 mg/ml to 0.5 mg/ml, or 0.01 mg/ml to 0.1 mg/ml.

In an embodiment, the plurality of monomers are in a solution comprising phosphate buffered saline (PBS), ammonium formate, or acetate. This mixture may optionally be purged with nitrogen. The purging with nitrogen may be for 1 min to 10 hours, 2 min to 1 hour, or about 5 min to 20 min.

In a particular embodiment, the plurality of monomers are included in a deoxygenated monomeric mixture which comprises NIPAM, methylene bisacrylamide (MBAA), tert-butylacrylamide, acrylic acid, 3-aminopropyl methacrylate, and PBS.

Many possible mixtures and combinations of monomers are possible, and the invention is not limited to the aforementioned. Any mixture of monomers, and any combination of concentrations, that would be suitable for forming a molecularly imprinted polymer would be suitable for use with the invention.

In some embodiments the monomer mixture preferably contains magnetic nanoparticles that are incorporated into the polymer. In some embodiments, polymer in the presence of target protein is formed by grafting onto a designated solid surface [14]. Grafting may comprise the attachment to any solid surface, for instance a surface comprising polysaccharide, silica, organic or inorganic polymer, metal, or a combination thereof. The solid surface may be of any form, for instance the form of the solid surface may be selected from beads, magnetic beads, arrays, the surface of waveguides, fibres, membranes, or capillaries.

In another embodiment, the target protein is preferably brought in contact with pre-formed polymer that has affinity to the target protein. In this case no additional polymerisation is required. The pre-formed polymer could be a MIP formed for a different protein, ligand or for part of protein-protein or protein-ligand complex. The ligand may be a small drug molecule, peptide, saccharide, protein, or other target known in the art.

The monomers are polymerised to create a protein:polymer complex with the target protein. The polymerisation of the monomers may be initiated chemically, thermally, or optically. The thermal initiation may be the application of heat. The optical initiation may be a photo-initiation. The optical initiation may be the use of UV or visible light. The polymer may be synthesised by free radical polymerisation living polymerisation, ionic polymerisation, or polycondensation. Several different forms of polymerisations are suitable for use with the present invention including bulk polymerisation, polymerisation in suspension and emulsion, precipitation polymerisation, living polymerisation, grafting or any other form known to practitioners in the art. The physical form of synthesised polymer can be solid particulate, layer or coating, powder or monolith, micro- or nanoparticles.

The optimal composition of monomer mixture and conditions of polymerisation reaction are these that preserve native structure of protein target. Some examples of living polymerisation include, but are not limited to: iniferter polymerisation, nitroxide-mediated polymerisation, atom-transfer radical polymerisation and reversible addition-fragmentation chain-transfer polymerisation. The advantage of living polymerization in contrast to traditional radical polymerization is that the former proceeds with a low rate producing nanoparticles with large contact area for interacting with protein.

The reaction conditions suitable for use with the presently disclosed methods for terminating the polymerisation reaction and leading to formation of polymer nano- and microparticles include, but are not limited to: (i) using stoichiometric ratio between initiator and monomers; (ii) cooling reaction or stopping UV or other irradiations; (iii) removal of the monomers from contact with the growing polymer chain by e.g. filtration or chromatography; (iv) adding inhibitors to the reaction; (v) performing polymerization in dilute solution.

Conventional free-radical generating polymerisation initiators may be employed to initiate polymerisation. Examples of suitable initiators include peroxides such as OO-t-amyl-O-(2ethylhexyl)monoperoxycarbonate, dipropylperoxydicarbonate, and benzoyl peroxide, as well as azo compounds such as azobisisobutyronitrile, 2,2'-azobis(2-amidinopropane)dihydrochloride, 2,2'-azobis(isobutyramide)dihydrate and 1,1'-azobis (cyclohexane carbonitrile). Examples of initiators include photo-iniferter bearing a dithiocarbamyl group, or azo compound. Other examples of suitable initiators include, but are not limited to: 2-bromo-propionitrile with Cu(I)Br complexed with N,N,N',N'',N''-pentamethyldiethylenetriamine, polystyrene bromo macro-initiator with Cu(I)Cl/PMDETA; ethyl 2-bromoisobutyrate with CuCl/bipyridine; 1,4-bis(2,6-diisopropylphenyl)acenaphatenediiminenickel (II) dibromide; 2,2-dimethoxy-2-phenylacephenone in combination with tetraethylthiuram disulfide; tetraphenyl biphosphine; tertiary peroxides such as di-tert-butyl peroxide; $SmMe(C_5Me_5)_2(THF)$; styrene-based epoxides in conjunction with $TiCl_4$; methylstyrene tetramer disodium; $MoOCl_4$-n-BuSn-EtOH; $HCl/ZnCl_2$; methyl p-toluenesulphonate; 2,10,15,20-tetraphenylporphinato aluminium methyl; 3-methyl-1,1-diphenylpentyllithium; butyllithium in THF; molybdenum alkylidine compounds; bifunctional organolanthanide(III); Mo(CH-t-Bu)(NAr)(OCMe3)2 and Mo(CHCPhMe2)(NAr)(OCMe(CF3)2)2; HI/I2; Zr, Ti and Hf complexes combined with either methylaluminoxane or phenyl borates; diimide complexes of Pd, Ni, Fe or Co; homogeneous Ta, Ti, Mo, W carbene complexes; rare earth metal complexes composed of metallocene type or non-metallocene type complexes; cationic monocyclopentadienyl zirconium acetamidinate complexes; esterified fluorinated telomers with one or two hydroxyl group as initiators for copper mediated living polymerisation; Yb[C(SiMe3)3]2.

The initiator can be present in the polymerisation mixture in an amount of from about 0.01 to 20% by weight of the monomers, preferably from 0.05 to 15%, or more preferably from 0.1 to 10% by weight of the monomers. The initiator is preferably present in the polymerisation mixture in an amount of from about 0.2 to 5% by weight of the monomers.

In a particular embodiment, an initiation solution can be used to initiate polymerisation of the plurality of monomers. This solution may comprise TEMED and/or ammonium persulfate (APS). TEMED may be at a concentration in an initiation solution of: 0.001 µg/mL to 1 mg/mL. APS may be at a concentration in an initiation solution of: 0.1 µg/µL to 1000 µg/µL.

The initiation solution may comprise PBS or other buffer salts. The role of buffer is to maintain or control intended conformation of protein target during polymerisation.

The polymer product may comprise particles with a mass of at least 100 Da, 500 Da, or 1000 Da. The polymer product may comprise particles with a mass of at least 10 kDa, 50 kDa, or 100 kDa.

The polymer product may comprise particles with a size 10 nm to 100 µm, 1 µm to 100 µm, 5 µm to 50 µm, 10 µm to 30 µm, or 15 µm to 25 µm. The preferred form of the polymer product is particles with size 500 Da-20 µm which could exist in soluble or colloidal forms.

In some embodiments, the polymer product may have a magnetic core. In some embodiments synthesised polymers are linear or cross-linked. In some embodiments, polymer is covalently linked to the target protein.

In an embodiment, the method may optionally further comprise, before the digestion of the protein in the protein:polymer complex to produce a peptide:polymer complex, the step of isolating the protein:polymer complex.

This isolation step may involve an increase in the purity or the concentration of the protein:polymer complex within a reaction mixture. Alternatively, the isolation step may include the separation of the protein:polymer complex from contaminants. In some embodiments the isolation step may include a washing step or washing steps. The isolation step may involve the separation of the protein:polymer complex from unreacted monomers and/or from free protein. In other embodiments the isolation step is not performed, or the isolation step does not involve the separation of the protein:polymer complex from unreacted monomers and/or from free protein.

In some embodiments the complex of protein with synthesised polymer is separated from unreacted monomers and other components or products of any preceding reaction by ultrafiltration, ultracentrifugation, electrophoresis, sonication, chromatographic separation, washing, adding urea, guanidine, by using magnetic forces, or any combination thereof. To facilitate separation of the polymer-protein complex from unbound monomers, the protein or polymer may be linked to a solid support (such as a bead or matrix, including a microarray or multi-well plate) (U.S. Pat. No. 6,365,418, ZYOMYX INC), and [15] or any other agent known in the art. Linking may be covalent or non-covalent. Methods for linking polymer or protein to solid support are well known in the art. In some embodiments the separation step is not required.

The method of the present invention comprises the step of digesting the protein in the complex to produce a peptide:polymer complex. The digestion may produce peptide fragments (e.g. epitopes) that are suitable for subsequent analysis, for instance, the peptide fragments might be suitable for subsequent sequencing. Digestion may be performed on the protein:polymer complex with or without separating the complex from unreacted monomers. The digestion may be a partial digestion. The partial digestion may be such that the peptide that is bound to the polymer is not digested. The partial digestion may be such that the parts of the protein that are not bound to the polymer are separated from the complex with the polymer. The digestion step may comprise the addition of one or more protein cleaving agent or may comprise a protein cleaving treatment. In some embodiments, the digestion may be performed chemically or enzymatically. The digestion may involve proteolysis, and may be mediated by one or more proteolytic catalyst, such as one or more protease. The digestion may be a partial proteolysis.

Examples of proteases that can be used as protein cleaving agents, include, but are not limited to, chymotrypsin, trypsin, thermolysin, V8 protease, Endoproteinases Factor Xa protease, thrombin, enterokinase, V5 protease, or the tobacco etch virus protease. The protein cleaving agent may be a chemical cleaving agent, such as a chemical substance or compound that cleaves polypeptides and peptide bonds. Non-limiting examples of chemical cleaving agents include cyanogen bromide and hydroxylamine. In still further embodiments, phosphatases (e.g., alkaline phosphatase, acid phosphatase, protein serine phosphatase, protein tyrosine phosphatase, protein threonine phosphatase, etc.), lipases, and other enzymes can be employed in addition to protein cleaving agents.

Microwaves can also be used to initiate protein cleaving. In some embodiments one protein cleaving agent is used. In other embodiments, more than one type of protein cleaving agent is used with respect to a single protein (e.g., two or more types of proteases or chemical cleaving agents), this may involve any combination of the aforementioned cleaving agents or treatments.

The form and conditions of the digestion step will depend on the protein cleaving agent chosen. The reaction conditions required for each protein cleaving agent are known in the art. The temperature and incubation time may be adjusted in accordance with standard techniques in the art.

The method comprises the step of isolating the peptide:polymer complex. This isolation step may involve an increase in the purity or concentration of the peptide:polymer complex within a reaction mixture. Alternatively, the isolation step may include the separation of the peptide:polymer complex from contaminants. In some embodiments the isolation step may include a washing step or washing steps. The isolation step may involve the separation of the peptide:polymer complex from unbound protein, unbound peptides, or cleaving agents. The isolation step may involve the separation from other components or products of the digestion step.

In some embodiments the complex of synthesised polymer with peptide fragments is separated from unbound peptides and cleaving agents and other components or products of the digestion step by ultrafiltration, ultracentrifugation, electrophoresis, sonication, chromatographic separation, washing, adding urea, guanidine, by using magnetic forces, or any combination thereof.

In a preferred embodiment, the method may further comprise, after the isolation of the peptide:polymer complex, a step of releasing bound peptide from the peptide:polymer complex. The releasing step may comprise eluting the bound peptide from the polymer. Examples of how to release the bound peptides include using conventional elution conditions such as change of temperature, pH, ionic strength, detergents, or any combination thereof. Optionally, peptides can be de-salted for subsequent sequencing analysis, depending on the subsequent sequencing technique utilised.

In some embodiments the separation step is not required. For instance, the peptide:polymer complex might be used directly in the step of the determination of the peptide sequence. In other embodiments, the released peptide may be suitable for use in a sequencing step or may be treated so as to be suitable for use in a sequencing step.

In some embodiments free protein is treated with a protein cleaving agent, whereby peptide fragments are generated. These fragments are brought in contact with synthesised polymer and allow formation of polymer-polypeptide complex. The unbound fragments are removed from the polymer by ultrafiltration, ultracentrifugation, electrophoresis, sonication, chromatographic separation, washing, adding urea, guanidine, by using magnetic forces, or any combination thereof. The bound peptides may be released from the polymer-peptides complex using conventional elution conditions such as change of temperature, pH, ionic strength, detergents, or any combination thereof. Generally, peptides can be de-salted for subsequent sequencing analysis.

The method of the invention may preferably include the step (iv) of sequencing the peptide. This sequencing step can be performed by any suitable method as peptide sequencing techniques are well known to those skilled in art. In some embodiments, the peptides may be sequenced by Edman degradation, mass spectrometry, mass spectrometry using matrix assisted laser desorption ionization (MALDI), electrospray ionization (ESI) sources, any atmospheric pressure ionisation techniques or tandem mass spectrometric analysis (MS/MS), any other suitable methods, or any combination thereof.

In some embodiments the peptide sequences are derived directly from the complex of polymer with peptides without the separation step and/or the release step. In other embodiments the sequence of the peptide is determined after release from the peptide:polymer complex.

In a preferred embodiment, there is provided a method for determining, on a protein, a binding site for a binding partner comprising:
contacting the protein with a plurality of monomers, and polymerising the monomers to create a protein:polymer complex;
digesting the protein in the complex to produce a peptide:polymer complex;
and isolating the peptide:polymer complex. The isolated peptide:polymer complex is a complex suitable for determining binding sites of the protein for binding partners.

In a most preferred embodiment, there is provided a method for determining, on a protein, a binding site for a binding partner, comprising:
contacting the protein with a plurality of monomers, and polymerising the monomers to create a protein:polymer complex;
isolating the protein:polymer complex;
digesting the protein in the complex to produce a peptide:polymer complex;
isolating the peptide:polymer complex;
releasing bound peptide from the peptide:polymer complex; and
sequencing the released peptide, wherein the released peptide corresponds to a binding site for a binding partner.

In a second aspect of the invention, there is provided use of a molecularly imprinted polymer (MIP) for producing a composition suitable for determining, on a protein, a novel binding site for a binding partner, optionally wherein the binding site is an epitope to which an antibody binds.

The use of the second aspect preferably comprises:
forming a protein:MIP complex;
digesting the protein in the complex to produce a peptide:MIP complex; and
isolating the peptide:MIP complex.

The peptide corresponds to a binding site for a binding partner.

The protein may be any as disclosed herein, for instance a folded protein, which may be in solution or immobilised on a solid surface. The solid surface may be of any composition or form as disclosed herein. For example, selected from a surface comprising polysaccharide, silica, organic or inorganic polymer, metal, or a combination thereof. The solid surface may be in any form, or a form selected from beads, magnetic beads, arrays, the surface of waveguides, fibres, membranes, or capillaries.

In an embodiment, the complex may be formed between a pre-formed MIP and the protein. The pre-formed polymer could be a MIP formed for a different protein, ligand or for part of a protein-protein or protein-ligand complex. The ligand may be a small drug molecule, peptide, saccharide, protein, or other target known in the aft.

In a preferred embodiment, the protein:MIP complex is formed by the contacting of the protein with a plurality of monomers, and then initiation of polymerisation of the monomers. The plurality of monomers may be any composition as disclosed herein, and preferably may include cross-linking monomers and/or magnetic nanoparticles.

The method of initiation, and any required reagents for initiation, may be any as disclosed herein. For instance, the polymerisation of the monomers may be initiated chemically; thermally, for instance by the use of heat; or optically, for instance the use of UV or visible light.

In an embodiment, the protein:MIP complex may be isolated before the digestion step. The method of isolation may be any as disclosed herein. For instance, by ultrafiltration, ultracentrifugation, electrophoresis, sonication, chromatographic separation, washing, adding urea, guanidine, by using magnetic forces, or any combination thereof.

In an embodiment, the digestion of the protein in the protein:MIP complex may comprise the partial proteolysis of the protein in the complex, such that the parts of the protein that are not bound to the polymer are separated from the complex with the polymer. The digestion step, and any required reagents, may take any form as disclosed herein. For instance, the digestion step may comprise the use of one or more protein cleaving agent, such as a protease.

The peptide:MIP complex is isolated after the digestion step. The method of isolation may be any as disclosed herein. For instance, by ultrafiltration, ultracentrifugation, electrophoresis, sonication, chromatographic separation, washing, adding urea, guanidine, by using magnetic forces, or any combination thereof.

In an embodiment, the bound peptide may be released from the peptide:MIP complex. This release may be by any method or form as disclosed herein. For instance, the release step may comprise releasing the bound peptide using elution conditions such as change of temperature, pH, ionic strength, detergents, or any combination thereof.

In an embodiment, the peptide:MIP or the released peptide may be utilised in a step for determining the sequence of the bound peptide. This step may comprise any sequencing method as described herein. For instance, the sequencing step may comprise the use of Edman degradation, mass spectrometry, mass spectrometry using matrix assisted laser desorption ionization (MALDI), electrospray ionization (ESI) sources, atmospheric pressure ionisation techniques or tandem mass spectrometric analysis (MS/MS), or any combination thereof.

In a preferred embodiment, there is provided the use of a molecularly imprinted polymer (MIP) for producing a composition suitable for determining, on a protein, a novel binding site for a binding partner, wherein the use comprises:
contacting of a target protein with a plurality of monomers, and the initiation of polymerisation of the monomers to form a protein:MIP complex;
isolating the protein:MIP complex;
digesting the protein in the complex to produce a peptide:MIP complex;
isolating the peptide:MIP complex;
releasing bound peptide from the peptide:MIP complex; and optionally sequencing the released peptide, wherein the released peptide corresponds to a binding site for a binding partner.

In a particular embodiment, there is provided the use of a pre-formed molecularly imprinted polymer (MIP) for producing a composition suitable for determining, on a protein, a novel binding site for a binding partner, wherein the use comprises:
contacting of a target protein or protein-ligand complex with a pre-formed MIP to form a protein:MIP or protein-ligand-MIP complex;

isolating the complex;

digesting the protein in the complex to produce a peptide:MIP complex;

isolating the peptide:MIP complex;

releasing bound peptide from the peptide:MIP complex; and optionally sequencing the released peptide, wherein the released peptide corresponds to a binding site for a binding partner.

In a third aspect of the invention, there is provided a kit for determining, on a protein, a binding site for a binding partner, the kit comprising:

a plurality of monomers suitable for contacting a target protein and polymerising the monomers to create a protein:polymer complex; and one or more protein cleaving agents.

In another embodiment, there is provided a kit for determining, on a protein, a binding site for a binding partner, the kit comprising components suitable for use with any of the methods of the present disclosure.

For instance, a kit may comprise components allowing the user to perform any method for determining, on a protein, a binding site for a binding partner, as disclosed herein.

Kits of the invention preferably include a monomer mixture suitable for contacting a target protein and polymerising the monomers to create a protein:polymer complex. The monomer mixture may comprise one type of monomer, two or more types of monomer, cross-linking monomers, or any combination thereof. The monomer mixture may comprise any of the plurality of monomers disclosed herein.

Optionally, the monomer mixture may comprise magnet nanoparticles or magnetic nanoparticles may be a separate component of the kit. The monomer mixture may be a suitable mixture for forming a molecularly imprinted polymer in complex with a target protein. The plurality of monomers may be supplied in a stable form to be combined with one or more solvent, solution, or buffer prior to use. The one or more solvent, solution, or buffer may also be included in the kit, or may not form part of the kit.

Optionally, the monomer mixture may comprise one or more initiator for initiating polymerisation or the one or more initiator may form a separate component of the kit. The one or more initiator may be any initiator or mixture of initiators disclosed herein. The initiator may be supplied in a stable form to be combined with one or more solvent, solution, or buffer prior to use. The one or more solvent, solution, or buffer may also be included in the kit, or may not form part of the kit.

The kit may optionally include materials comprising a solid surface suitable for the immobilisation of the target protein. The solid surface may be any composition as disclosed herein. For example, selected from a surface comprising polysaccharide, silica, organic or inorganic polymer, metal, or a combination thereof. The solid surface may be of any form as disclosed herein. For example in a form selected from beads, magnetic beads, arrays, the surface of waveguides, fibres, membranes, or capillaries.

Kits of the invention may optionally comprise one or more protein cleaving agents. The protein cleaving agent may be any of the protein cleaving agents disclosed herein, for example one or more enzyme or one or more chemical cleaving agent. The one or more enzyme may be a protease, for example trypsin.

The protein cleaving agent may comprise one or more appropriate buffer, solvent, or solution. The one or more solvent, solution, or buffer may be separate from the other components of the protein cleaving agent, for instance an enzyme and suitable buffer may form separate components of the kit. Alternatively, one or more solvent, solution, or buffer may not be supplied with the kit.

The kit may optionally further comprise materials for isolation or purification. The kit may comprise materials for use in the isolation of a protein:polymer complex or for use in the isolation of a peptide:polymer complex. The kit may optionally comprise materials for ultrafiltration and/or centrifugation. For instance, the kit may comprise one or more filter or centrifuge filter (e.g. a centrifugation cartridge with appropriate filtration membrane). One or more filter may be a 20 kDa to 1 µm centrifuge filter, or preferably 50 kDa centrifuge filter. The kit may include columns, for example columns for use in purification or desalting of compositions, or analytical columns.

The kit may optionally comprise magnets and/or containers suitable for the magnetic isolation of compositions or the magnetic purification of compositions.

The kit may comprise buffers or solutions for use in the method of the invention. For instance, the kit may comprise one or more solutions or buffers suitable to form the conditions suitable for contacting a target protein with a plurality of monomers and polymerising monomers to create a protein:polymer complex. The kit may comprise one or more solutions or buffers suitable for performing the digestion of the protein in the protein:polymer complex to produce a peptide:polymer complex. The kit may comprise one or more solutions or buffers suitable for isolating the protein:polymer complex. The kit may comprise one or more solutions or buffers suitable for isolating the peptide:polymer complex. The kit may comprise one or more solutions or buffers suitable for the elution of the peptide from the peptide:polymer complex. The kit may comprise one or more solutions or buffers suitable for preparing the peptide:polymer complex or the released peptide for subsequent sequencing.

One or more of the solutions or buffers may comprise, consist essentially of, or consist of salts useful for maintaining intended conformation of protein target and not preventing peptide sequences, such as ammonium and formic acid. One or more of the solutions or buffers may comprise, consist essentially of, or consist of PBS, ammonium formate, or acetate. One or more of the solutions or buffers may comprise, consist essentially of, or consist of water, for example ultrapure water and/or LC-MS grade water. One or more of the solutions or buffers may comprise formic acid, the formic acid maybe be at a concentration of 0.01% to 1%, 0.05% to 0.5%, or preferably approximately 0.1%. One or more of the formic acid buffers may comprise LC-MS grade water. One or more of the formic acid buffers may comprise acetonitrile.

In some embodiments, the kit may comprise instructions for use of the kit components in accordance with any of the methods of the invention described herein. The kit may be in suitable packaging. Suitable packaging includes, but is not limited to, vials, bottles, jars, flexible packaging (e.g., sealed Mylar or plastic bags), and the like. In some embodiments, the kit comprises a container and a label or package insert(s) on or associated with the container. The kit may comprise one or more container suitable for use as a reaction vessel for any of the method steps disclosed herein.

In a preferred embodiment, the kit may comprise:

a plurality of monomers suitable for contacting a target protein and polymerising the monomers to create a protein:polymer complex;

an initiator, suitable for initiating polymerisation;
one or more protein cleaving agents, including one or more enzymes; and
one or more cartridge, suitable for use in an isolation step.

The kit may optionally further comprise:
one or more buffers

The kit may optionally further comprise:
labels and instructions.

In a fourth aspect of the invention, there is provided compositions and products designed using information derived from peptide sequencing.

Once a potential binding site has been identified, binding partners can be designed and produced using known techniques. For instance, the method of the invention may lead to the identification of an epitope suitable for the binding of potential antibodies, and an antibody to this site can be producing using routine techniques. Alternatively, MIPs may be generated that bind to the identified binding site. The target protein can be a medically relevant protein, thus the newly designed binding partners may be relevant for use in medicine.

In one embodiment, identified peptide sequences are used to design immunogens, for instance immunogens comprising 4 to 20 amino acids. In some embodiments identified peptide sequences are used to produce antibodies (e.g., human, humanized, mouse, rabbit, chimeric, etc). Antibodies may be produced by a number of methods known in the art, including, for example production by a hybridoma, recombinant production, or using animals. Immunogens may be produced by chemical synthesis using methods well known in the art. In some embodiments peptides are used to produce MIPs, aptamers, affimers or other natural or synthetic receptors. In some embodiments of present invention information about peptide sequences or peptide sequences themselves are used in, but not limited to, diagnostics and therapeutic applications, personalised medicine, imaging, drug delivery, vaccine development or proteomics research.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which.

EXAMPLES

Figure 1:
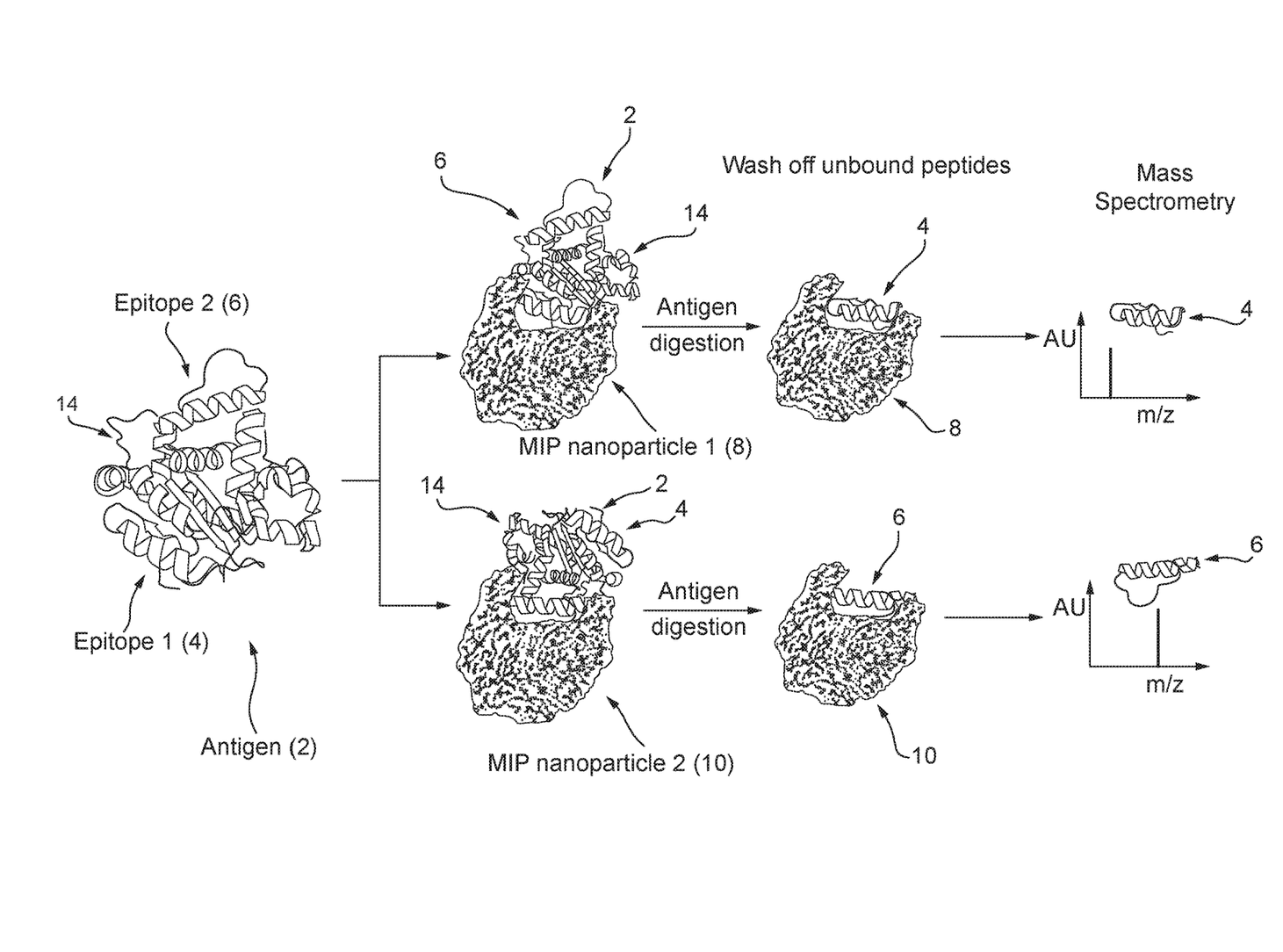
FIG. 1 shows a schematic representation of an embodiment of the methods of the invention. The embodiment shown uses molecular imprinting and mass spectrometry for the identification of peptide sequences exposed on a protein surface.

The present invention will now be further described particularly with references to the following non-limiting examples, and FIG. 1.

Example 1

Epitope Mapping Using Molecularly Imprinted Polymers

Referring to FIG. 1, there is shown an antigen 2, which can be any proteinaceous material, such as a protein or polypeptide. The antigen 2 has two epitopes 4, 6, which are exposed on the surface of an inner region 14, and it is these epitopes 4, 6 which the method seeks to identify as binding sites of a binding partner, such as an antibody, aptamer, affimer, small drug molecule, MIP or other natural or synthetic receptor. Sequence information for these epitopes 4, 6 can be obtained using molecular imprinting and sequencing techniques. Knowledge about these amino acid sequences may be subsequently used for generating binding partners, such as high affinity antibodies, or other natural or synthetic receptors, for research, diagnostic, or therapeutic applications.

In one embodiment of the method, the antigen 2 is contacted with a plurality of monomers, which are then polymerised to create a molecularly imprinted polymer (MIP) nanoparticle 8, which complexes with epitope 4 such that epitope 6 is exposed (see top of FIG. 1). The resulting complex is shown as MIP nanoparticle 8. In the same reaction vessel, the antigen 2 is also contacted with a plurality of monomers, which are then polymerised to create a molecularly imprinted polymer (MIP) nanoparticle 10, which complexes with epitope 6 such that epitope 4 is exposed (see bottom of FIG. 1). The resulting complex is shown as MIP nanoparticle 10.

Following creation of the two MIP nanoparticles 8, 10, the antigen 2 is digested with an enzyme, which digests off either the inner region 14 and epitope 6 leaving just epitope 4 complexed with the MIP nanoparticle 8 (see top of FIG. 1), or the inner region 14 and epitope 4 leaving just epitope 6 complexed with MIP nanoparticle 10 (see bottom of FIG. 1). The epitope:MIP complexes 8, 10 can then be analysed using mass spectrometry to determine the sequences of epitope 4 and epitope 6.

Example 2

Epitope Mapping of AChE

To demonstrate the method described in Example 1, the target for identification of peptide epitope sequences on a protein surface was acetylcholine esterase (AChE) enzyme from electric eel *Electrophorus electricus* (Sigma, C-3389). 4.4 mg of the AChE was dissolved in 2 mL of PBS. 0.7 mL of sample was mixed with 10 mL of the deoxygenated monomeric mixture (19.5 mg of NIPAM, 3 mg of methylene bisacrylamide (MBAA), 15 mg of tert-butylacrylamide, 50 µL, of the solution of 22 µL of acrylic acid in 1 mL of $H_2O$, and 3 mg of 3-aminopropyl methacrylate dissolved in 50 mL of phosphate buffered saline (PBS) and purged with nitrogen for 20 min) and polymerisation initiated by adding 100 µL of freshly prepared solution of 12 mg of ammonium persulfate (APS) and 6 µL of TEMED dissolved in 400 µL of PBS. The polymerisation was carried out for 1 h at a room temperature (20° C.). In order to remove the unreacted functional monomers and low-affinity particles, the polymerised samples were filtered through the 50 kDa centrifuge filter for 30 min at a 3500 rpm. 10 mL of PBS were added, incubated for 10 min and passed through centrifuge filter as described above.

MIP nanoparticles bound to protein were reconstituted in 5 mL of PBS containing 0.5 mg of trypsin (Bovine pancrease, Sigma, T9201) and incubated at a room temperature for 36 h. Free fragments of digested AChE and trypsin were removed by centrifugation of the samples using 50 kDa centrifuge cartridge for 15 min at a 3500 rpm followed by 2×5 mL wash with PBS. The peptides bound to MIPs were separated from polymers using 2×1 mL of hot water, lyophilised and reconstituted in 0.1% formic acid. The peptides were initially loaded onto a Waters 2G-V/M Symmetry C18 trap column (180 μm×20 mm, 5 μm) to desalt and chromatographically focus the peptides prior to elution onto a Waters Acquity HSS T3 analytical UPLC column (75 μm×250 mm, 1.8 μm). Single pump trapping was used with 99.9% solvent A and 0.1% solvent B at flow rate of 5 μL/min for 3 min. Solvent A was LC-MS grade water containing 0.1% formic acid and solvent B was acetonitrile containing 0.1% formic acid.

Table 1 shows the peptide sequences that are the most prevalent (≥40% peak intensity) in the I-TASSER model [16] found using molecular imprinting and mass spectrometry. The sequence identified here matches these found using the Immune Epitope Database and Analysis Resource (IEDB) search tool http://www.iedb.org [17]. The imprinting method has correctly identified two out of three known epitopes. Four other sequences have not been previously identified as epitopes for acetylcholine esterase.

TABLE 1

Peptide sequences that are the most prevalent (≥40% peak intensity) in the I-TASSER model found using molecular imprinting and mass spectrometry and these found using the Immune Epitope Database and Analysis Resource (IEDB).

| Peptide sequence location | Peptide sequence in I-TASSER MODEL found using molecular imprinting and mass spectrometry | Peptide Sequences found in epitope database (IEDB) |
|---|---|---|
| 200-217 | LALQWVQDNIHFFGGNPK (SEQ ID NO: 1) | |
| 313-320 | FRFSFVPV (SEQ ID NO: 2) | FRFSFVPV (human) (SEQ ID NO: 7) |
| 218-243 | QVTIFGESAGAASVGMHLLSPDSRPK (SEQ ID NO: 3) | GESAGAA$^{12}$ (eel) (SEQ ID NO: 8) |
| 375-382 | EDFLQGVK (SEQ ID NO: 4) | |
| 526-532 | | YWANFAR (human) (SEQ ID NO: 9) |
| 533-547 | TGNPNINVDGSIDSR (SEQ ID NO: 5) | |
| 549-559 | RWPVFTSTEQK (SEQ ID NO: 6) | |

For the analytical column, the flow rate was set at 0.3 μL/min and the temperature maintained at 40° C. The 50 min run time gradient elution was initiated as the peptides were eluted from the trap column. The following gradient was used: 0 min-3% B, 30 min-40% B, 32 min-85% B, 40 min-85% B and 41 min-3% B. The NanoAcquity UPLC was coupled to a Waters Synapt G2 HDMS mass spectrometer. The instrument was operated in positive electrospray ionisation (ESI) mode. The capillary voltage was set at 2.4 kV and cone voltage at 30 V. PicoTip emitters (New Objective, US, 10 μm internal diameter) were used for the nanostage probe. A helium gas flow of 180 mL/min and ion mobility separator nitrogen gas flow of 90 mL/min with a pressure of 2.5 mbar were used. The IMS wave velocity was set at 650 m/s and the IMS wave height at 40 V.

During the HDMSE acquisition a low collision induced dissociation (CID) energy of 4V was applied across the transfer ion guide. For the high CID energy acquisition a ramp of 20 to 40 V was applied. Argon was used as the CID gas. Lockspray provided mass accuracy throughout the chromatographic run using [Glu1]-Fibrinopeptide (GFP) with 785.8427 m/z. The data was acquired using MassLynx 4.1. All raw data were processed using ProteinLynx Global SERVER (PLGS) (Waters Corporation, Milford, Massachusetts, USA). PLGS was used to assemble the data for alignment, peak picking, peptide and protein identification and limited upstream statistics. Data was searched against Uniprot *Electrophorus electricus* database (downloaded December 2016).

Example 3

Epitope Mapping of AChE Using Magnetic Beads 19.5 mg of NIPAM, 3 mg of methylene bisacrylamide (MBAA), 15 mg of tert-butylacrylamide, 50 μL of the solution of 22 μL of acrylic acid in 1 mL of $H_2O$, 3 mg of 3-aminopropyl methacrylate were dissolved in 50 mL of phosphate buffered saline (PBS) and purged with nitrogen for 20 min. Before the polymerisation 10 mg of the iron oxide nanoparticles (10-30 nm diameter), modified with 3-(trimethoxysilyl) propyl methacrylate, were added to 10 mL of the monomeric mixture and purged with nitrogen for 5 min. 5 mg of AChE (Sigma, C-3389) was solubilised in 10 mL of monomeric mixture and purged for 5 min with nitrogen. The polymerisation was initiated by adding 100 μL of freshly prepared solution of 12 mg of ammonium persulfate (APS) and 6 μL of TEMED dissolved in 400 μL of PBS. The polymerisation was carried out for 1 h at a room temperature (20° C.).

Magnetic material was collected using magnet and washed 3×10 mL of PBS. Collected magnetic materials with bound AChE were treated by adding 10 mL of the solution of 1 mg of trypsin (Bovine pancrease, Sigma, T9201) in PBS and incubating at a room temperature (20° C.) for 3 days. The magnetic particles bound to peptides were collected using magnet and washed 3×10 mL of the cold water. The specific peptides were eluted from magnetic particles using 3×1 mL of hot water (90° C.). The eluted peptides were sequenced as described in Example 1.

Example 4

Analysis of Sequences of AChE Epitopes Identified by Molecular Imprinting

Only four of the *Electrophorus electricus* (Ee) AChE sequences: 200-217 LALQWVQDNIHFFGGNPK (SEQ ID No:1), 218-243 QVTIFGESAGAASVGMHLLSPDSRPK (SEQ ID No:3), 313-320 FRFSFVPV (SEQ ID No:2) and 526-532 YWANFAR (SEQ ID No:9) have matches with human (h) AChE. Parts of these sequences are known epitopes for anti-AChE antibodies [18-20].

The following sequences: 209-215 (hAChE) LALQWVQ (SEQ ID No:10), 231-247 (hAChE) FGESAGAASVGMHLLSP (SEQ ID No:11), 326-333 (hAChE) FRFSFVPV (SEQ ID No:7), and 526-532 (hAChE) YWANFAR (SEQ ID No:9) are identical for both EeAChE and hAChE.

TABLE 2

Peptide sequences identified in MIP, and their correlation with known epitopes

| Sequence identified in molecular imprinting work | Sequence of known epitope [1-3] |
|---|---|
| LALQWVQDNIHFFGGNPK (SEQ ID No: 1) | LLDQRLALQW (SEQ ID No: 12) |
| QVTIFGESAGAASVGMHLLSPDSRPK (SEQ ID No: 3) | TLFGESAGAA (SEQ ID No: 13); KTVTIFGESAGGASVGMHILSPGSR (SEQ ID No: 14) |
| FRFSFVPV (SEQ ID No: 7) | VFRFSFVPV (SEQ ID No: 15) |
| EDFLQGVK (SEQ ID No: 4) | |
| YWANFAR (SEQ ID No: 9) | YWANFAR (SEQ ID No: 9) |
| TGNPNINVDGSIDSR (SEQ ID No: 5) | |
| RWPVFTSTEQK (SEQ ID No: 6) | |

Example 5

Synthesis and Characterisation of MIP Nanoparticles for Epitopes Identified for AChE The corresponding peptides, including a linker consisting of two glycine residues and a terminal cysteine were first synthesised for use as templates and immobilized onto the surface of amine derivatized glass beads. A solid-phase approach described by Canfarotta et al. [21] was adapted for MIP nanoparticle synthesis. The affinity of nanoMIPs imprinted against each epitope of AChE was assessed using a surface plasmon resonance (SPR) instrument (MP-SPR Navi 220A NAALI). For these experiments, MIP nanoparticles were covalently immobilized onto the sensor surface and a kinetic titration performed, increasing concentration of protein with each injection. All MIPs exhibited excellent affinity for AChE, with $K_D$ values in the low nanomolar range (Table 3). Importantly, MIP nanoparticles synthesised for epitope present mainly in denatured AChE were able to bind to native AChE (Table 3).

TABLE 3

Affinity of MIP nanoparticles synthesised using epitopes identified for AChE

| Epitope used in synthesis of MIP nanoparticles | $K_D$ of synthesised MIP nanoparticles to native AChE |
|---|---|
| YWANFAR (SEQ ID No: 9) MS Intensity*-45% in both, native and denatured protein | 4.04 nM |
| FGESAGAASVGMHLLSP (SEQ ID No: 11) MS intensity-86% in native protein, 10% in denatured | 0.85 nM |

TABLE 3-continued

Affinity of MIP nanoparticles synthesised using epitopes identified for AChE

| Epitope used in synthesis of MIP nanoparticles | $K_D$ of synthesised MIP nanoparticles to native AChE |
|---|---|
| FRFSFVPV (SEQ ID No: 7) MS intensity-100% in denatured protein, 10% in native protein | 26.3 pM |
| LALQWVQ (SEQ ID No: 10) MS intensity-100% in both, native and denatured protein | 0.84 M |

*relative percentage of peptide intensity in MS spectrum

CONCLUSIONS

Advantages of the invention reside in the ability to experimentally determine peptide sequences that are binding sites, without prior knowledge of the protein, protein structure, or any candidate binding sites. Thus, the method may be used to identify completely novel binding sites. Furthermore, the invention does not require the use of complex reagents, such as antibodies, which may be either unavailable or challenging to produce due to complexity, expense, and/or the time required.

REFERENCES

1. Imai, K., Takaoka, A. 2006 *Nature Reviews Cancer,* 6 (9), 714.
2. Ahmad, T. A., Eweida, A. E., Sheweita, S. A. 2016 *Trials in Vaccinology,* 5, 71.
3. Points to Consider in the Manufacture and Testing of Monoclonal Antibody Products for Human Use, U.S. Food and Drug Administration, Docket No. 94D-0259.
4. Gershoni, J. M., Roitburd-Berman, A., Siman-Tov, D. D., Freund, N. T., Weiss, Y. 2007, *BioDrugs,* 21 (3), 145.
5. Abbott, W. M., Damschroder, M. M., Lowe, D. C. 2014, *Immunology,* 142 (a), 526.
6. Conte, L. L., Chothia, C., Janin, J. 1999, *Journal of Molecular Biology,* 285 (5), 2177
7. Suckau, D., Köhl, J., Karwath, G., Schneider, K., Casaretto, M., Bitter-Suermann, D., Przybylski, M. 1990, Proceedings of the National Academy of Sciences of the United States of America, 87 (24), 9848.
8. Ansari, H. R., Raghava, G. P. S. 2013, *Methods in Molecular Biology,* 993, 129
9. Mandell, J. G., Roberts, V. A., Pique, M. E., Kotlovyi, V., Mitchell, J. C., Nelson, E., Tsigelny, I., Ten Eyck, L. F. 2001, *Protein Engineering,* 14 (2), 105.
10. Schneidman, E., Still, S., Berry II, M. J., Bialek, W. 2003, *Physical Review Letters,* 91 (23), 2387011.
11. Kulkarni-Kale, U., Bhosle, S., Kolaskar, A. S. 2005, *Nucleic Acids Research,* 33 (SUPPL. 2).
12. Rubinstein, N. D., Mayrose, I., Martz, E., Pupko, T. 2009, *BMC Bioinformatics,* 10, art. no. 1471, p. 287
13. Tai, D. F.; Ho, Y. F.; Wu, C. H.; Lin, T. C.; Lu, K. H.; Lin, K. S. *Analyst,* 2011, 136, 11, 2230.
14. Piletsky, S. A., Piletska, E. V., Chen, B., Karim, K., Weston, D., Barrett, G., Lowe, P., Turner, A. P. F. 2000, *Analytical Chemistry,* 72 (18), 4381.
15. Kennedy, J. H., Kricka, L. J., Wilding, P. 1976, *Clinica Chimica Acta,* 70 (1), 1.
16. Yang, J., Yan, R., Roy, A., Xu, D., Poisson, J., Zhang, Y. 2014, *Nature Methods,* 12 (1), 7.
17. Vita, R., Overton, J. A., Greenbaum, J. A., Ponomarenko, J., Clark, J. D., Cantrell, J. R., Wheeler, D. K., Gabbard, J. L., Hix, D., Sette, A., Peters, B. 2015, *Nucleic Acids Research,* 43 (D1), D405.
18. Hashimoto M., Rockenstein E., Crews L., Masliah E. (2003). Role of protein aggregation in mitochondrial dysfunction and neurodegeneration in Alzheimer's and Parkinson's diseases. Neuromolecular Med., 4, 21-36.
19. Talesa, V. N. Mechanisms of Ageing and Development 2001, 122, 1961-1969.
20. Perry, E. K.; Tomlinson, B. E.; Blessed, G.; Bergmann, K.; Gibson, P. H.; Perry, R. H. British Medical Journal, 1978, 2, 1457-1459.
21. Canfarotta F., Poma A., Guerreiro A., Piletsky A. (2016). Solid-phase synthesis of molecularly imprinted nanoparticles (MIP NPs) for diagnostic applications. Nature Protocols, 11, 443-455.

The invention claimed is:

1. A method for determining, on a protein, a binding site for a binding partner, comprising:
  contacting the protein with a plurality of monomers;
  polymerising the monomers to create a protein:polymer complex;
  digesting the protein in the complex to produce a peptide: polymer complex; and
  isolating the peptide:polymer complex
  wherein the peptide corresponds to a binding site for a binding partner.

2. The method of claim 1, comprising sequencing the peptide.

3. The method of claim 1, wherein the protein is a folded protein and/or wherein the binding site is a novel binding site, optionally wherein the binding site is an epitope to which an antibody binds.

4. The method of claim 1, wherein a complex between the protein and a molecularly imprinted polymer (MIP) is created by contacting the protein with the plurality of monomers and polymerising the monomers to create the protein:polymer complex.

5. The method of claim 1, wherein the plurality of monomers comprises cross-linking monomers, or magnetic nanoparticles.

6. The method of claim 1, wherein the protein contacted with a plurality of monomers is in solution or immobilised on a solid surface, and the solid surface is selected from the group consisting of polysaccharide, silica, organic or inorganic polymer, metal, and a combination thereof, and/or the form of the solid surface is selected from beads, magnetic beads, arrays, the surface of waveguides, fibres, membranes, or capillaries.

7. The method of claim 1, wherein the polymer product:
  (a) has a magnetic core;
  (b) is linear or cross-linked;
  (c) is covalently linked to the target protein; and/or
  (d) is in a soluble or colloidal form.

8. The method of claim 1, further comprising the step:
  isolating the protein:polymer complex, optionally wherein the isolation of the protein:polymer complex comprises the use of ultrafiltration, ultracentrifugation, electrophoresis, sonication, chromatographic separation, washing, adding urea, guanidine, magnetic forces, or any combination thereof, and/or
  wherein the protein or polymer is linked to a solid support to facilitate the isolation of the protein:polymer complex.

9. The method of claim 1, wherein digesting the protein is a partial proteolysis reaction, such that the parts of the protein that are not bound to the polymer are separated from the complex with the polymer, optionally comprising the use of one or more protein cleaving agent.

10. The method of claim 1, wherein isolating the peptide: polymer complex comprises the separation of the peptide: polymer complex from unbound protein and/or unbound peptide, optionally wherein comprising the use of ultrafiltration, ultracentrifugation, electrophoresis, sonication, chromatographic separation, washing, adding urea, guanidine, magnetic forces, or any combination thereof.

11. The method of claim 1, further comprising the step: releasing bound peptide from the peptide:polymer complex.

12. The method of claim 2, wherein sequencing the peptide comprises the use of Edman degradation, mass spectrometry, mass spectrometry using matrix assisted laser desorption ionization (MALDI), electrospray ionization (ESI) sources, atmospheric pressure ionisation techniques or tandem mass spectrometric analysis (MS/MS), or any combination thereof.

13. The method of claim 1, wherein the plurality of monomers comprises one or more monomer selected from the group consisting of: vinyl monomers, allyl monomers, acetylenes, acrylates, methacrylates, acrylamides, methacrylamides, chloroacrylates, itaconates, trifluoromethylacrylates, derivatives of amino acids, nucleosides, nucleotides, carbohydrates, ethylene glycol dimethacrylate, trimethylolpropane trimethacrylate, divinylbenzene, methylene bisacrylamide, ethylene bisacrylamide and N,N'-bisacryloylpiperazine, N-Isopropylacrylamide (NIPAM), tert-butylacrylamide, acrylic acid, 3-aminopropyl methacrylate, methacrylic acid, and any combination thereof.

* * * * *